United States Patent
Bhirud et al.

(10) Patent No.: US 10,106,483 B2
(45) Date of Patent: Oct. 23, 2018

(54) PROCESS FOR PREPARATION OF AZELAIC ACID

(71) Applicant: Glenmark Pharmaceuticals Limited, Mumbai (IN)

(72) Inventors: Shekhar Bhaskar Bhirud, Mumbai (IN); Kumar Hari Bhushan, Haryana (IN); Prem Chand, Navi Mumbai (IN); Amit Anant Thanedar, Nashik (IN); Amol Anant Kadam, Mumbai (IN); Krishna Baban Narawade, Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/521,046

(22) PCT Filed: Oct. 21, 2015

(86) PCT No.: PCT/IB2015/058101
§ 371 (c)(1),
(2) Date: Apr. 21, 2017

(87) PCT Pub. No.: WO2016/067160
PCT Pub. Date: May 6, 2016

(65) Prior Publication Data
US 2017/0334825 A1    Nov. 23, 2017

(30) Foreign Application Priority Data
Oct. 29, 2014 (IN) .................. 3420/MUM/2014

(51) Int. Cl.
*C07C 51/43* (2006.01)

(52) U.S. Cl.
CPC .................... *C07C 51/43* (2013.01)

(58) Field of Classification Search
CPC ........ C07C 51/43; C07C 51/083; C07C 51/44
See application file for complete search history.

(56) References Cited

U.S. PATENT DOCUMENTS

| | | | | |
|---|---|---|---|---|
| 2,998,439 A * | 8/1961 | Manley | ............. | C11C 1/007 |
| | | | | 554/207 |
| 3,402,108 A | 9/1968 | Oehlschlaeger et al. | | |
| 6,660,505 B2 * | 12/2003 | Staley | ............. | C07C 51/48 |
| | | | | 435/136 |
| 2003/0032825 A1 * | 2/2003 | Gaige | ............. | C07C 51/48 |
| | | | | 554/121 |

FOREIGN PATENT DOCUMENTS

| | | |
|---|---|---|
| CN | 1970524 A | 5/2007 |
| WO | 0068346 A1 | 11/2000 |
| WO | WO0068346 | * 11/2000 |
| WO | 2012103325 A2 | 8/2012 |

OTHER PUBLICATIONS

Zhou et al., "Study on the process for separation and purification of high purity azelaic acid", Huaxue Shiji, vol. 29, Issue 7, pp. 443-446 (Original) (Year: 2007).*

Zhou et al., "Study on the process for separation and purification of high purity azelaic acid", Huaxue Shiji, vol. 29, Issue 7, pp. 1-14, English Translation (Year: 2007).*

* cited by examiner

*Primary Examiner* — Pancham Bakshi
*Assistant Examiner* — Mark R Luderer
(74) *Attorney, Agent, or Firm* — Ryan, Mason & Lewis, LLP

(57) ABSTRACT

Provided is a process for preparing azelaic acid.

12 Claims, 2 Drawing Sheets

Glenmark Pharmaceuticals Limited

PROCESS FOR PREPARATION OF AZELAIC ACID

PRIORITY

This application claims priority under 35 U.S.C. § 371 to International Application No. PCT/IB2015/058101, filed Oct. 21, 2015 which claims the benefit of Indian Provisional Application 3420/MUM/2014 filed Oct. 29, 2014, and entitled "PROCESS FOR PREPARATION OF AZELAIC ACID", the contents of which are incorporated herein by reference.

FIELD OF THE INVENTION

The present invention relates to a novel process for preparation of azelaic acid.

BACKGROUND OF THE INVENTION

Azelaic acid is marketed as AZELEX™ AND FINACEA™. Chemically, azelaic acid is nonane dioic acid .i.e it is a $C_9$ aliphatic dicarboxylic acid.

Processes for preparation of azelaic are known in the art. The present invention provides a novel process for preparation of azelaic acid which provides a better purity profile and which can be easily performed on industrial scale.

SUMMARY OF THE INVENTION

The present invention provides a process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an acid; and
b) followed by treatment with a hydrocarbon solvent and an ester solvent.

DETAILED DESCRIPTION OF THE INVENTION

Figure 1:
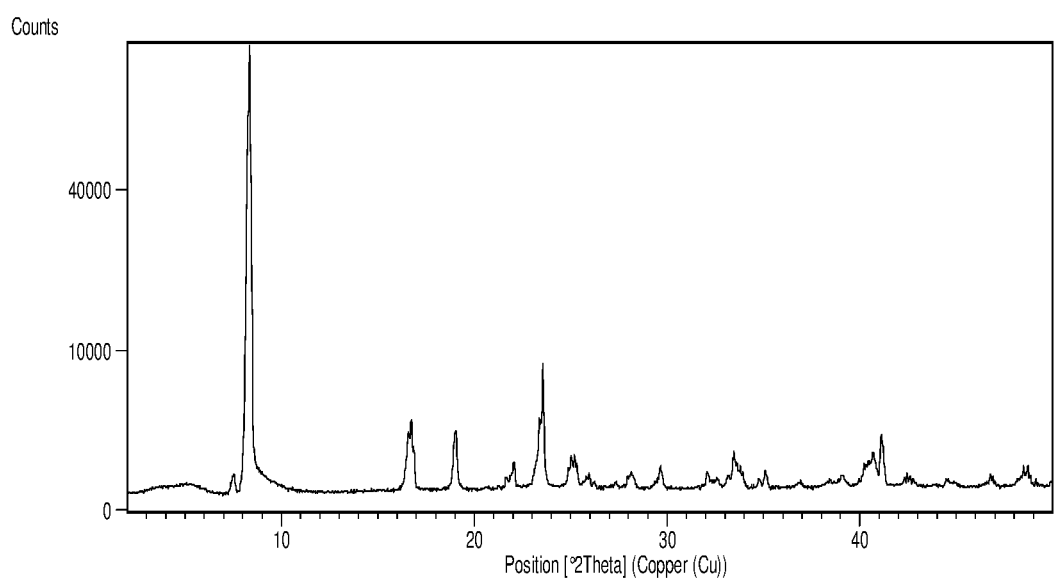
FIG. 1 is XRPD of crystalline form of azelaic acid prepared as per example 3.

The present invention provides a process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an acid; and
b) followed by treatment with a hydrocarbon solvent and an ester solvent.

In one embodiment, the present invention provides a process for the preparation of azelaic acid, wherein the level of total impurities is less than about 1% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an acid; and
b) followed by treatment with a hydrocarbon solvent and an ester solvent.

In one embodiment, the present invention provides a process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC; and the level of total impurities is less than about 1% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an acid; and
b) followed by treatment with a hydrocarbon solvent and an ester solvent.

In one embodiment, the present invention provides azelaic acid, wherein the level of total impurities is less than about 1% w/w with respect to azelaic acid as measured by HPLC.

In one embodiment, the level of total impurities may be less than about 0.5% w/w with respect to azelaic acid as measured by HPLC.

In one embodiment, the level of total impurities may be less than about 0.1% w/w with respect to azelaic acid as measured by HPLC, preferably less than about 0.05% w/w with respect to azelaic acid as measured by HPLC.

In one embodiment, the $C_3$-$C_{18}$ aliphatic mono carboxylic acid may be saturated aliphatic monocarboxylic acid, or unsaturated aliphatic monocarboxylic acid optionally substituted with hydroxy group.

In one embodiment, the $C_3$-$C_{18}$ saturated aliphatic mono carboxylic acid may be propanoic acid, hexanoic acid, nonanoic acid, palmitic acid or stearic acid.

In one embodiment, the $C_3$-$C_{18}$ unsaturated aliphatic mono carboxylic acid may have more than one C=C units.

In one embodiment, the $C_3$-$C_{18}$ unsaturated aliphatic mono carboxylic acid may be oleic acid, linoleic acid, linolenic acid or ricinoleic acid.

In one embodiment, the $C_3$-$C_8$ aliphatic dicarboxylic acid may be malonic acid, adipic acid, pimelic acid or suberic acid.

In one embodiment, the $C_3$-$C_8$ aliphatic dicarboxylic acid may be pimelic acid or suberic acid.

In one embodiment, the $C_{10}$-$C_{18}$ aliphatic dicarboxylic acid may be sebacic acid, undecane dioic acid, dodecanedioc acid, tridecanedioic acid or tetradecane dioic acid.

In one embodiment, the $C_{10}$-$C_{18}$ aliphatic dicarboxylic acid may be sebacic acid or undecanedioic acid.

In one embodiment, the $C_{1-5}$ alkyl ester of azelaic acid may be monomethyl azelate or diethyl azelate.

In one embodiment, "crude azelaic acid" used in (a) refers to azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is greater than about 0.15% w/w with respect to azelaic acid as measured by HPLC.

In one embodiment, "crude azelaic acid" used in (a) refers to azelaic acid wherein, the total purity is about 50-99% as measured by HPLC.

In one embodiment, crude azelaic acid used in (a) may be prepared by various processes known in the art.

In one embodiment, crude azelaic acid used in (a) may be prepared by a process comprising oxidation of ricinoleic acid.

Oxidizing agents used may include potassium permanganate, iron (II) chromate, zirconium oxide-molybdenum oxide, vanadium oxide clusters, Jone's reagent, osmium (VIII) oxide, cetyl pyridinium peroxotungstophosphate-dihydrogenperoxide, sodium periodate.

In one embodiment, oxidation of ricinoleic acid may be performed by treating ricinoleic acid with potassium permanganate in presence of a base. The base used may be an inorganic or organic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may include an amine which may be a primary, secondary or a tertiary amine. Examples of organic base include methylamine, ethylamine, triethylamine, propylamine, isopropylamine, diisopropylamine, tertiary butylamine and the like.

In one embodiment, the base used is an alkali metal hydroxide, preferably potassium hydroxide.

In one embodiment, the present invention provides a process wherein crude azelaic acid used in (a) may be prepared by a process comprising oxidation of ricinoleic acid with potassium permanganate in presence of a base.

In one embodiment, the present invention provides a process wherein crude azelaic acid used in (a) may be prepared by a process comprising oxidation of ricinoleic acid with potassium permanganate in presence of potassium hydroxide.

In one embodiment, the potassium permanganate is used in the form of an aqueous solution.

In one embodiment, the aqueous solution of potassium permanganate is cooled to a temperature of about 10-20° C., preferably 15° C. before treatment with ricinoleic acid.

In one embodiment, the aqueous solution of potassium permanganate may be treated with alkaline solution of ricinoleic acid at a temperature of about 10-35° C. The reaction mass obtained may be heated to a temperature of about 35-55° C. and then cooled to a temperature of about 15-25° C. Reaction mass obtained may be treated with an acid at a temperature of about 55-85° C. Solid obtained maybe filtered off and the filtrate obtained may be cooled to a temperature of about 0-15° C. and filtered. Wet cake obtained may be washed with water and dried to obtain crude azelaic acid.

In one embodiment, "crude azelaic acid" used in step (a) comprises reaction mixture obtained after oxidation of ricinoleic acid.

In one embodiment, "crude azelaic acid" used in step (a) comprises the isolated crude azelaic acid after removal of solvents optionally, followed by drying.

In one embodiment, treating crude azelaic acid containing one or more impurities with an acid in (a) comprises, slurring crude azelaic acid with acid, or washing crude azelaic acid with acid, or adding crude azelaic acid to an acid, heating and optionally cooling, or dissolution of crude azelaic acid in acid at higher temperature optionally followed by cooling.

In one embodiment, the treatment of crude azelaic acid with an acid in (a), may be performed more than once.

The acid used for treating crude azelaic acid in step (a) may be an organic or inorganic acid.

The organic acid used may include an acid such as formic acid, acetic acid, citric acid, tartaric acid, bitartaric acid, benzoic acid, lactic acid, malic acid, fumaric acid, succinic acid, gluconic acid, pamoic acid, methanesulfonic acid, benzenesulfonic acid and the like. The inorganic acid used may include an acid such as hydrochloric acid, hydrobromic acid, hydroiodic acid, nitric acid, phosphoric acid, sulfuric acid, trifluoroacetic acid, and the like.

In one embodiment, the acid used may be concentrated acid.

In one embodiment, the concentrated acid may be diluted with water.

In one embodiment, the dilution of concentrated acid may be done by mixing concentrated acid with water in the range 1-2:0.5-1 (v/v).

In one embodiment, the acid used is inorganic acid, preferably nitric acid.

In one embodiment, the product obtained in (a) may be isolated.

In one embodiment, the product obtained in (a) may not be isolated and the reaction mixture obtained after treatment with nitric acid may be used for next step.

In one embodiment, the product obtained in (a) may, after isolation, optionally be treated with water wherein treatment with water comprises, slurring with water, or washing with water, or adding the product to water, heating and optionally cooling, or dissolution at higher temperature optionally followed by cooling.

In one embodiment, the product may be isolated after optional water treatment by methods known in the art.

In one embodiment, in (a), crude azelaic acid may be treated with aqueous nitric acid followed by heating the reaction mass obtained to a temperature of about 60-90° C. Reaction mass obtained may be cooled to a temperature of about 0-15° C. and filtered. Wet cake obtained may be added to water and the reaction mass may be heated to a temperature of about 60-90° C. and further cooled to a temperature of about 0-15° C. and dried.

In one embodiment, treatment in (b) comprises washing with a hydrocarbon solvent and an ester solvent, or slurring with a hydrocarbon solvent and an ester solvent, or recrystallizing with a hydrocarbon solvent and an ester solvent, or adding to a hydrocarbon solvent and an ester solvent, heating and optionally cooling, or dissolution in a hydrocarbon solvent and ester solvent at higher temperature optionally followed by cooling.

In one embodiment, treatment in (b) comprises washing the product isolated after treatment with acid in (a) with a hydrocarbon solvent and an ester solvent, or slurring the product isolated after treatment with acid in (a) with a hydrocarbon solvent and an ester solvent, or recrystallizing the product isolated after treatment with acid in (a) with a hydrocarbon solvent and an ester solvent, or adding the product isolated after treatment with acid in (a) to a hydrocarbon solvent and an ester solvent, heating and optionally cooling, or dissolution of the product isolated after treatment with acid in (a) in a hydrocarbon solvent and an ester solvent at higher temperatures optionally followed by cooling.

In one embodiment, the treatment in (b), with a hydrocarbon solvent and an ester solvent may be performed more than once.

In one embodiment, treatment in (b) comprises washing reaction mixture obtained after treatment with acid with (a) a hydrocarbon solvent and an ester solvent, or slurring reaction mixture obtained after treatment with an acid in (a) with a hydrocarbon solvent and an ester solvent, or adding reaction mixture obtained after treatment with acid in (a) to a hydrocarbon solvent and an ester solvent, heating and optionally cooling.

In one embodiment, treatment in (b) comprises recrystallizing the product isolated in step (a) with a hydrocarbon solvent and an ester solvent.

In one embodiment, treatment in (b) comprises adding the product isolated in step (a) to a hydrocarbon solvent and an ester solvent, heating to a temperature of about 55-85° C., followed by cooling.

In one embodiment, the hydrocarbon solvent in (b) may be aliphatic hydrocarbons such as hexane, heptane, cyclohexane and the like; aromatic hydrocarbons such as toluene, xylene, chlorobenzene and the like.

In one embodiment, the ester solvent in (b) may include esters such as methyl acetate, ethyl acetate, propyl acetate, butyl acetate, tert-butyl acetate and the like.

In one embodiment, the hydrocarbon solvent may be cyclohexane and the ester solvent may be ethyl acetate.

In one embodiment, the hydrocarbon solvent may be added to the product isolated in step (a) after addition of ester solvent, or may be added to the product isolated in step (a) before addition of ester solvent.

In one embodiment, the hydrocarbon solvent may be added to the reaction mixture obtained after treatment with acid in (a) after addition of ester solvent, or may be added to reaction mixture obtained after treatment with acid in (a) before addition of ester solvent.

In one embodiment, the hydrocarbon and ester solvent may be used as a mixture.

In one embodiment, treatment in (b) comprises recrystallizing the product isolated in step (a) with a mixture of hydrocarbon solvent and an ester solvent.

In one embodiment, treatment in (b) comprises recrystallizing the product isolated in step (a) with a mixture of cyclohexane and ethyl acetate.

In one embodiment, treatment in (b) comprises recrystallizing the product isolated in step (a) with a mixture of cyclohexane and ethyl acetate in the ratio of 0.5-1.2:0.3-0.8 (v/v).

In one embodiment, treatment in (b) comprises adding the product isolated in step (a) to a mixture of cyclohexane and ethyl acetate, heating to temperature of about 55-85° C., followed by cooling.

In one embodiment, the recrystallization from a hydrocarbon solvent and an ester solvent may be performed more than once.

In one embodiment, the product obtained after recrystallization in step (b) may optionally be treated with water wherein treatment with water comprises, slurring with water, or washing with water, or adding the product to water, heating and optionally cooling, or dissolution of product in water at higher temperatures optionally followed by cooling.

In one embodiment, the product may be isolated after recrystallization or optional water treatment by methods known in the art.

In one embodiment, the present invention provides a process for the preparation of azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an acid; and
b) followed by treatment with a hydrocarbon solvent and an ester solvent.

In one embodiment, the present invention provides a process for the preparation of azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an inorganic acid; and
b) followed by treatment with a hydrocarbon solvent and an ester solvent.

In one embodiment, present invention provides a process for the preparation of azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with an inorganic acid; and
b) followed by treatment with cyclohexane and ethyl acetate.

In one embodiment, present invention provides a process for the preparation of azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, comprising
a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with nitric acid; and
b) followed by treatment with cyclohexane and ethyl acetate.

In one embodiment, the present invention provides a process for the preparation of azelaic acid wherein, the level of any single impurity selected from the group consisting of propanoic acid, hexanoic acid, nonanoic acid, palmitic acid, stearic acid, oleic acid, linoleic acid, linolenic acid, ricinoleic acid, malonic acid, adipic acid, pimelic acid, suberic acid, sebacic acid, undecane dioic acid, dodecanedioc acid, tridecanedioic acid, tetradecane dioic acid, monomethyl azelate and diethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with inorganic acid; and b) followed by treatment with a hydrocarbon solvent and an ester solvent In one embodiment, the present invention provides a process for the preparation of azelaic acid wherein, the level of any single impurity selected from the group consisting of propanoic acid, hexanoic acid, nonanoic acid, palmitic acid, stearic acid, oleic acid, linoleic acid, linolenic acid, ricinoleic acid, malonic acid, adipic acid, pimelic acid, suberic acid, sebacic acid, undecane dioic acid, dodecanedioc acid, tridecanedioic acid, tetradecane dioic acid, monomethyl azelate and diethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with inorganic acid; and b) followed by treatment with cyclohexane and ethyl acetate.

In one embodiment, the present invention provides a process for the preparation of azelaic acid wherein, the level of any single impurity selected from the group consisting of propanoic acid, hexanoic acid, nonanoic acid, palmitic acid, stearic acid, oleic acid, linoleic acid, linolenic acid, ricinoleic acid, malonic acid, adipic acid, pimelic acid, suberic acid, sebacic acid, undecane dioic acid, dodecanedioc acid, tridecanedioic acid, tetradecane dioic acid, monomethyl azelate and diethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with nitric acid; and b) followed by treatment with cyclohexane and ethyl acetate.

In one embodiment, the present invention provides a process for the preparation of azelaic acid wherein, the level of any single impurity selected from the group consisting of pimelic acid, suberic acid, sebacic acid, undecane dioic acid and monomethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with inorganic acid; and b) followed by treatment with a hydrocarbon solvent and an ester solvent.

In one embodiment, the present invention provides a process for the preparation of azelaic acid wherein, the level of any single impurity selected from the group consisting of pimelic acid, suberic acid, sebacic acid, undecane dioic acid and monomethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with inorganic acid; and b) followed by treatment with cyclohexane and ethyl acetate.

In one embodiment, the present invention provides a process for the preparation of azelaic acid wherein, the level of any single impurity selected from the group consisting of pimelic acid, suberic acid, sebacic acid, undecane dioic acid and monomethyl azelate, is less than about 0.15% w/w with respect to azelaic acid as measured by HPLC, comprising a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters with nitric acid; and b) followed by treatment with cyclohexane and ethyl acetate In one embodiment, step (b) involves treatment of product obtained in (a) with a mixture of cyclohexane and ethyl acetate at a temperature of about 55-85° C. The reaction mass may then be cooled to room temperature and filtered. Recrystallization step may be repeated if required. Product obtained may be added to water and the reaction mass may be heated to about 70-95° C., filtered to get a filtrate which may be heated to 70-95° C. and cooled to about 15-35° C., filtered and dried.

In one embodiment, the present invention provides a process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids; and $C_{1-5}$ alkyl esters of azelaic acid, is less than about 0.5% w/w with respect to azelaic acid as measured by HPLC, comprising treating crude azelaic acid containing one or more impurities with an acid. The acid used is as discussed supra.

In one embodiment, the present invention provides azelaic acid free of any single impurity selected from the group consisting of pimelic acid, suberic acid, sebacic acid, undecane dioic acid and monomethyl azelate.

In one embodiment, the treatment of crude azelaic acid containing one or more impurities, with an acid may be performed more than once.

In one embodiment, "crude azelaic acid", as used here, refers to azelaic acid wherein, the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is greater than about 0.5% w/w with respect to azelaic acid as measured by HPLC.

In one embodiment, "crude azelaic acid", as used here, refers to azelaic acid wherein, the purity of azelaic acid is about 50-99% as measured by HPLC.

The preparation of crude azelaic acid is as discussed supra.

"$C_3$-$C_{18}$ aliphatic mono carboxylic acids", "$C_3$-$C_8$ aliphatic dicarboxylic acids", "$C_{10}$-$C_{18}$ aliphatic dicarboxylic acids", and "$C_{1-5}$ alkyl esters of azelaic acid are as discussed supra".

In one embodiment, "crude azelaic acid", as used here, comprises reaction mixture obtained after oxidation of ricinoleic acid.

In one embodiment, "crude azelaic acid" as used here, comprises the isolated crude azelaic acid after removal of solvents optionally followed by drying.

In one embodiment, treating crude azelaic acid containing one or more impurities with an acid comprises, slurring crude azelaic acid with acid, or washing crude azelaic acid with acid, or adding crude azelaic acid to an acid, heating and optionally cooling, or dissolution of crude azelaic acid in acid at higher temperature optionally followed by cooling.

In one embodiment, the present invention provides a process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids; and $C_{1-5}$ alkyl esters of azelaic acid, is less than about 0.5% w/w with respect to azelaic acid as measured by HPLC, comprising treating crude azelaic acid containing one or more impurities with nitric acid.

In one embodiment, the treatment of crude azelaic acid containing one or more impurities, with nitric acid may be performed more than once.

In one embodiment, in (a), crude azelaic acid may be treated with aqueous nitric acid followed by heating the reaction mass obtained to a temperature of about 60-90° C. Reaction mass obtained may be cooled to a temperature of about 0-15° C. and filtered. Wet cake obtained may be added to water and the reaction mass may be heated to a temperature of about 60-90° C. and further cooled to a temperature of about 0-15° C. and dried.

In one embodiment, the present invention provides a crystalline form of azelaic acid.

In one embodiment, the present invention provides a crystalline form of azelaic acid characterized by an X-ray powder diffraction pattern with peaks expressed in degrees 2θ±0.2° θ at about 8.32, 19.0 and 28.15.

In one embodiment, the present invention provides a crystalline form of azelaic acid characterized by an X-ray powder diffraction pattern with peaks expressed in degrees 2θ±0.2° θ at about 8.25, 8.36, 16.75, 23.36 and 23.55.

In one embodiment, the present invention provides a crystalline form of azelaic acid characterized by an X-ray powder diffraction pattern with peaks expressed in degrees 2θ±0.2° θ at about 8.25, 8.36, 16.75, 16.88, 19.06, 23.36, 23.55, 33.48, 40.69 and 41.10.

In one embodiment, the present invention provides a crystalline form of azelaic acid characterized by an X-ray powder diffraction pattern with peaks expressed in degrees 2θ±0.2° θ at about 3.38, 5.07, 7.55, 8.25, 8.36, 16.56, 16.75, 16.88, 19.06, 21.63, 22.07, 23.36, 23.55, 25.02, 25.20, 25.95, 26.23, 27.34, 28.15, 29.66, 32.08, 32.62, 33.16, 33.48, 33.93, 34.77, 35.09, 36.95, 38.36, 39.07, 40.21, 40.44, 40.69, 41.10, 42.44, 42.61, 44.47, 46.77, 48.49, 48.71, 49.12.

In one embodiment, the present invention provides a crystalline form of azelaic acid characterized by X-ray powder diffraction pattern which is substantially in accordance with FIG. 1.

Figure 2:
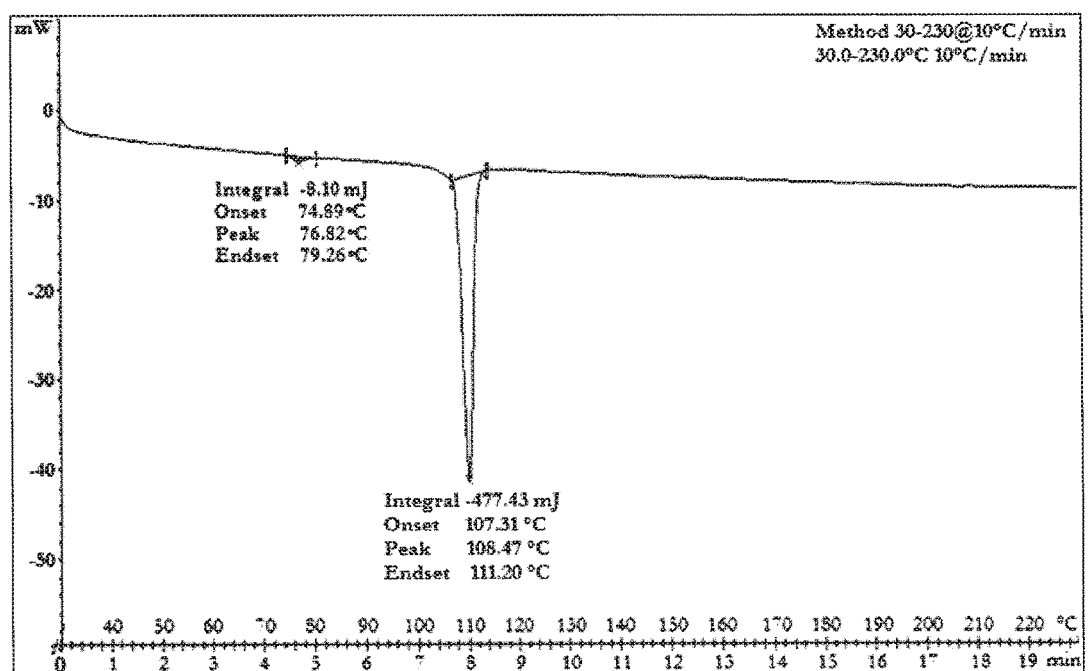
FIG. 2 is DSC thermogram of crystalline form of azelaic acid prepared as per example 3.

In one embodiment, the present invention provides a crystalline form of azelaic acid characterized by differential scanning calorimetry endotherm curve, which is substantially in accordance with FIG. 2.

In one embodiment, the present invention provides a crystalline form of azelaic acid characterized by differential scanning calorimetry endotherm curve having an endothermic peak at about 108.0±3° C.

The present invention provides azelaic acid as characterized and analyzed by following techniques:

A. X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator [1]; Scanning Mode; Active length (2Theta)=2.122°; generator 45 KV; tube current 40 mAmp. The samples were scanned in the full 2θ range of 2-50° with a "time-per-step" 50 seconds.

B. DSC (Mettler Toledo 822e): Temperature range is "30° C. to 230° C." and heating rate is 10° C./minute.

C. PSD: Particle size analysis was performed on Malvern Mastersizer 2000 with Sample handling unit 'Hydro2000S (A)' using 2% Lecithin solution prepared in isopar-G dispersant.

D. Water determination, in the present invention, was done by Karl Fischer methodology employing the following process:

The titration vessel was filled with the 15-20 ml of methanol. The start button was pressed. After the display shows 'drift OK', parameters were changed to 'KFT' mode and started. About 30.0 mg of water was added and the weight was entered and the start button was pressed. Burette reading was noted from the display after completion of the titration. K.F. Factor was calculated using the formula:

K.F. Factor=(weight of water in mg/Burette reading)

The instrument was then changed to 'KF mode'. The start button was pressed. About 100 mg of the test sample was transferred into the titration vessel and the sample weight was entered. Enter button was pressed. After completion of titration burette reading was noted from the display Water content of the test sample was calculated using the following equation:

a. Burette reading×K.F. Factor

Water Content (%)= - - - ×100 b. Weight of sample in mg

In one embodiment, the present invention provides a process for preparation of crystalline form of azelaic acid comprising treating azelaic acid with a hydrocarbon solvent and an ester solvent.

In one embodiment, the treatment of azelaic acid with a hydrocarbon solvent and an ester solvent may be performed more than once.

In one embodiment, treating azelaic acid with a hydrocarbon solvent and an ester solvent comprises washing azelaic acid with a hydrocarbon solvent and an ester solvent, or slurring azelaic acid with a hydrocarbon solvent and an ester solvent, or recrystallizing azelaic acid with a hydrocarbon solvent and an ester solvent, or adding azelaic acid to a hydrocarbon solvent and an ester solvent, heating and optionally cooling, or dissolution of azelaic acid in a hydrocarbon solvent and an ester solvent at higher temperatures optionally followed by cooling.

In one embodiment, treating azelaic acid with a hydrocarbon solvent and an ester solvent comprises recrystallizing azelaic acid with a hydrocarbon solvent and an ester solvent.

In one embodiment, treating azelaic acid with a hydrocarbon solvent and an ester solvent comprises adding azelaic acid to a hydrocarbon solvent and an ester solvent, heating to temperature of about 55-85 C, followed by cooling.

In one embodiment, hydrocarbon solvent may include aliphatic hydrocarbons such as hexane, heptane, cyclohexane and the like; aromatic hydrocarbons such as toluene, xylene, chlorobenzene and the like In one embodiment, the ester solvent may include esters such as methyl acetate, ethyl acetate, propyl acetate, butyl acetate, tert-butyl acetate and the like.

In one embodiment, the hydrocarbon solvent may be cyclohexane and the ester solvent may be ethyl acetate.

The hydrocarbon solvent may be added to azelaic acid after addition of ester solvent, or may be added to azelaic acid before addition of ester solvent.

In one embodiment, the hydrocarbon and ester solvent may be used as a mixture.

In one embodiment, treating azelaic acid with a hydrocarbon solvent and an ester solvent comprises recrystallizing the azelaic acid with a mixture of hydrocarbon solvent and an ester solvent.

In one embodiment, treating azelaic acid with a hydrocarbon solvent and an ester solvent comprises recrystallizing the azelaic acid with a mixture of cyclohexane and ethyl acetate.

In one embodiment, treating azelaic acid with a hydrocarbon solvent and an ester solvent comprises adding azelaic acid to a mixture of cyclohexane and ethyl acetate, heating to temperature of about 55-85° C., followed by cooling.

In one embodiment, the present invention provides a process for the preparation of crystalline form of azelaic acid comprising adding azelaic acid to a mixture cyclohexane and ethyl acetate at a temperature of 65-75° C., followed by cooling.

In one embodiment, the present invention provides a process for the preparation of crystalline form of azelaic acid comprising treating azelaic acid with a mixture of cyclohexane and ethyl acetate.

The product obtained after treatment with a hydrocarbon and an ester solvent may be isolated and dried by processes known in the art.

In one embodiment, the present invention provides a process for the preparation of crystalline form of azelaic acid comprising treating azelaic acid with a mixture cyclohexane and ethyl acetate at a temperature of 60-80° C.

In one embodiment, the azelaic acid obtained after recrystallization may optionally be treated with water wherein treatment with water comprises, slurring with water, or washing with water, or adding the product to water, heating, and optionally cooling, or dissolution of product in water optionally followed by cooling.

In one embodiment, the product may be isolated after recrystallization or optional water treatment by methods known in the art.

In one embodiment, the present invention provides a process for preparation of crystalline form of azelaic acid comprising treating azelaic acid with a mixture of ethyl acetate and cyclohexane at a temperature of about 55-85° C. The reaction mass may then be cooled to room temperature and filtered. Recrystallization step may be repeated if required. The product obtained may be added to water and the reaction mass may be heated to about 70-95° C., filtered to get a filtrate which may be heated to 70-95° C. and cooled to about 15-35° C., filtered and dried.

In one embodiment, the present invention provides azelaic acid with water content less than 1% w/w as measured by Karl Fischer titration.

In one embodiment, the present invention provides pharmaceutical compositions comprising azelaic acid or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns.

In one embodiment, the present invention provides azelaic acid obtained by the processes herein described having $D_{90}$ particle size of less than about 16 microns and $D_{50}$ particle size of less than about 8 microns.

The particle size disclosed here can be obtained by, for example, any milling, grinding, micronizing or other particle size reduction method known in the art to bring the solid state azelaic acid into any of the foregoing desired particle size range.

In one embodiment, the present invention provides azelaic acid having a purity of at least 99% as measured by HPLC and, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids; and $C_{1-5}$ alkyl esters of azelaic acid, is less than about 0.15% w/w with respect to azelaic acid as measured by HPLC.

In one embodiment, the present invention provides azelaic acid having a purity of at least 99.5% as measured by HPLC and, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC.

In one embodiment, the present invention provides crystalline form of azelaic acid having particle size distribution with D90 of about 30 μm after jet milling.

In one embodiment, the present invention provides azelaic acid having a purity of 99.95% as measured by HPLC. HPLC method used for determination of purity is described below:

Apparatus: A High Performance Liquid Chromatograph equipped with quaternary gradient pumps, variable wavelength UV detector attached with data recorder and integrator software.
Column: YMC-Pack pro C18, 250×4.6 mm, 5μ
Column temperature: 30° C.
Mobile phase A: Buffer
Buffer: 3.4 g Potassium dihydrogen phosphate in 1000 ml water. pH adjusted to 2.8 with o-Phosphoric acid.
Mobile phase B: Acetonitrile

| Time (min.) | % Mobile Phase A | % Mobile Phase B |
| --- | --- | --- |
| 0.01 | 90 | 10 |
| 03 | 90 | 10 |
| 30 | 50 | 50 |
| 70 | 50 | 50 |
| 75 | 90 | 10 |
| 80 | 90 | 10 |

Diluent: Acetonitrile:Isopropylalcohol:Water (50:25:25, v/v/v) Flow Rate: 1 mL/minute,
Detection: UV 210 nmInjection Volume: 20 μL The examples that follow are provided to enable one skilled in the art to practice the invention and are merely illustrative of the invention. The examples should not be read as limiting the scope of the invention as defined in the features and advantages.

EXAMPLES

Example 1 (Preparation of Ricinoleic Acid)

500 g of castor oil was added to a solution of 100 g of potassium hydroxide in 1 liter of methanol and refluxed at a temperature of about 60-70° C. for about 3 hrs. The solution was then poured into water and acidified with concentrated sulfuric acid. Reaction mass was heated to about 65-75° C. and stirred. Aqueous layer was separated and oily mass was washed with water at about 65-75° C. and sodium chloride solution. Oily mass was unloaded at 55-60° C. Yield 400 g-475 g.

Example 2 (Preparation of Crude Azelaic acid)

About 17.3% (w/v) aqueous potassium permanganate was taken in a round-bottomed flask, stirred and cooled to about 15° C. To it an alkaline solution of ricinoleic acid (prepared by dissolving 270 g of the product obtained in example 1 in aq potassium hydroxide) was added at about 15-30° C. with stirring. The reaction mass was heated to about 40-45° C. for about 1 hr, cooled to about 20° C., acidified with sulfuric acid, and heated to about 65-75° C. for about one hour and filtered hot. Inorganic solid obtained was suspended into water and the mass was stirred at about 65-75° C. for about 1 hr and filtered hot to filter off the inorganic solid again. The filtrates obtained after filtering off the inorganic solid were combined, cooled, stirred and filtered to obtain a wet cake which was washed with water and dried.

Wet cake obtained was added to aq nitric acid and the reaction mass was heated to about 70-80° C., stirred, cooled and filtered. Product obtained was washed with water and dried. Wet cake obtained was added to water, heated at about 70-80° C., stirred, cooled and filtered. Solid obtained was washed with water, suck dried and further dried in air oven to get azelaic acid.

| Impurity name | HPLC % | | Limit of Detection |
|---|---|---|---|
| | Before HNO3 treatment | After HNO3 treatment | |
| Malonic acid | 0.22 | Not detected | 0.003% |
| Pimelic acid | 0.08 | Not detected | 0.004% |
| Suberic acid | 0.39 | 0.02 | 0.003% |
| RRT0.95 (unidentified impurity) | 3.90 | 0.01 | |
| Sebacic acid | 0.12 | 0.04 | 0.002% |
| hexanoic acid | 0.10 | 0.01 | 0.005% |
| Undecanedioic acid | 0.28 | 0.15 | 0.002% |
| Azelaic acid monomethyl ester | 0.19 | 0.09 | 0.001% |
| Dodecanedioic acid | 0.97 | 0.39 | 0.003% |
| tetradecanedioic acid | 0.09 | Not detected | 0.001% |
| nonanoic acid | 0.14 | Not detected | 0.006% |

Example 3 (Purification of Azelaic Acid)

140 gm of crude azelaic acid obtained after following process of example 2 was added to a mixture of cyclohexane and ethyl acetate (1:0.6-0.7 v/v) and the reaction mass was heated to about 65-75° C. The reaction mass was cooled to room temperature, stirred, filtered and the solid obtained was dried. The recrystallization step may be repeated if required. Wet cake obtained was washed with cyclohexane and dried at about 50-55° C. under vacuum for about 12 hrs. Product obtained was added to purified water, heated to about 80-85° C. for about 30 min, filtered hot through micron filter. Filtrate obtained was heated to about 80-85° C. for about 30 min, cooled to room temperature, stirred, filtered and dried. Wet cake obtained was washed with purified water and dried in air tray dryer at about 60-70° C. for about 12 hrs. (Yield—113 gm, HPLC purity >99.7%, water content by Karl Fischer <1% w/w).

Particle Size Distribution after Jet Milling

| D (0.1) | D (0.5) | D (0.9) |
|---|---|---|
| 2.6µ | 7.3µ | 19.5µ |

| Impurity name | Azelaic acid prepared in example 2 | Azelaic acid prepared in example 3 |
|---|---|---|
| Pimelic acid | Not detected | Not detected |
| Suberic acid | Not detected | Not detected |
| Sebacic acid | 0.07 | 0.01 |
| Undecanedioic acid | 0.30 | 0.04 |
| Azelaic acid monomethyl ester | 0.01 | Not detected |
| dodecanedioic acid | 0.19 | Not detected |

The invention claimed is:

1. A process for the preparation of azelaic acid, wherein the level of any single impurity selected from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid, is less than about 0.15% w/w with respect to azelaic acid as measured by HPLC, the process comprising
    (a) treating crude azelaic acid containing one or more impurities from the group consisting of $C_3$-$C_{18}$ aliphatic mono carboxylic acids, $C_3$-$C_8$ aliphatic dicarboxylic acids, $C_{10}$-$C_{18}$ aliphatic dicarboxylic acids, and $C_{1-5}$ alkyl esters of azelaic acid with an acid; and
    (b) treating the treated crude azelaic acid of step (a) with a hydrocarbon solvent and an ester solvent, wherein the hydrocarbon solvent is cyclohexane and the ester solvent is ethyl acetate.

2. The process as claimed in claim 1, wherein the level of total impurities is less than about 1% w/w with respect to azelaic acid as measured by HPLC.

3. The process as claimed in claim 1, wherein treating step (b) comprises washing with a hydrocarbon solvent and an ester solvent, or slurring with a hydrocarbon solvent and an ester solvent, or recrystallizing with a hydrocarbon solvent and an ester solvent, or adding to a hydrocarbon solvent and an ester solvent, heating and optionally cooling, or dissolving in a hydrocarbon solvent and ester solvent at a higher temperature optionally followed by cooling, wherein the hydrocarbon solvent is cyclohexane and the ester solvent is ethyl acetate.

4. The process as claimed in claim 1, wherein the $C_3$-$C_{18}$ aliphatic mono carboxylic acid is a saturated aliphatic monocarboxylic acid or an unsaturated aliphatic monocarboxylic acid optionally substituted with hydroxy group.

5. The process as claimed in claim 1, wherein the $C_3$-$C_{18}$ unsaturated aliphatic monocarboxylic acid is selected from the group consisting of oleic acid, linoleic acid, linolenic acid and ricinoleic acid.

6. The process as claimed in claim 4, wherein the $C_3$-$C_{18}$ saturated aliphatic mono carboxylic acid is selected from the group consisting of propanoic acid, hexanoic acid, nonanoic acid, palmitic acid and stearic acid.

7. The process as claimed in claim 1, wherein the $C_3$-$C_8$ aliphatic dicarboxylic acid is selected from the group consisting of malonic acid, adipic acid, pimelic acid and suberic acid.

8. The process as claimed in claim 1, wherein the $C_{10}$-$C_{18}$ aliphatic dicarboxylic acid is selected from the group consisting of sebacic acid, undecane dioic acid, dodecanedioc acid, tridecanedioic acid and tetradecane dioic acid.

9. The process as claimed in claim 1, wherein the $C_{1-5}$ alkyl ester of azelaic acid is selected from the group consisting of monomethyl azelate and diethyl azelate.

10. The process as claimed in claim 1, wherein any single impurity selected from the group consisting of pimelic acid, suberic acid, sebacic acid, undecanedioc acid and azelaic acid monomethyl ester in the azelaic acid obtained by the process of claim 1 is not more than 0.15% w/w with respect to azelaic acid as measured by HPLC.

11. The process as claimed in claim 1, wherein the acid used in step (a) is an organic or inorganic acid.

12. The process as claimed in claim 1 wherein the acid used in step (a) is an inorganic acid.

\* \* \* \* \*